(12) United States Patent
Bhagchandani (10) Patent No.: US 9,125,801 B2
(45) Date of Patent: Sep. 8, 2015

(54) VISUAL INFLATION/DEFLATION INDICATOR FOR A BALLOON CATHETER

(71) Applicant: Cook Medical Technologies LLC, Bloomington, IN (US)

(72) Inventor: Neha S. Bhagchandani, Newport Beach, CA (US)

(73) Assignee: Cook Medical Technologies, LLC, Bloomington, IN (US)

( * ) Notice: Subject to any disclaimer, the term of this patent is extended or adjusted under 35 U.S.C. 154(b) by 116 days.

(21) Appl. No.: 13/947,165

(22) Filed: Jul. 22, 2013

(65) Prior Publication Data

US 2014/0074021 A1    Mar. 13, 2014

Related U.S. Application Data

(60) Provisional application No. 61/700,056, filed on Sep. 12, 2012.

(51) Int. Cl.
*A61M 29/00* (2006.01)
*A61J 15/00* (2006.01)
*A61M 25/10* (2013.01)

(52) U.S. Cl.
CPC .......... *A61J 15/0042* (2013.01); *A61J 15/0065* (2013.01); *A61M 25/10187* (2013.01); *A61J 2015/0088* (2013.01)

(58) Field of Classification Search
CPC ........ A61J 2015/0088; A61J 15/003–15/0049; A61M 25/10184; A61M 25/10187; A61M 25/10188
USPC ........ 604/100.01, 100.03, 99.01, 103.13, 514
See application file for complete search history.

(56) References Cited

U.S. PATENT DOCUMENTS

| | | | |
|---|---|---|---|
| 3,543,759 A | 12/1970 | McWhorter | |
| 4,266,550 A | 5/1981 | Bruner | |
| 4,361,107 A | 11/1982 | Gereg | |
| 6,364,867 B2 | 4/2002 | Wise et al. | |
| 6,394,093 B1 | 5/2002 | Lethi | |
| 6,530,898 B1 | 3/2003 | Nimkar et al. | |
| 6,705,320 B1 | 3/2004 | Anderson | |
| 6,878,130 B2 | 4/2005 | Fournie et al. | |
| 7,018,359 B2 | 3/2006 | Igarashi et al. | |
| 7,052,481 B2 | 5/2006 | Fawcett | |
| 7,470,248 B1 | 12/2008 | Connelly et al. | |
| 8,033,176 B2 | 10/2011 | Esnouf | |
| 8,142,394 B1 | 3/2012 | Rotella et al. | |
| 8,177,742 B1 | 5/2012 | Bagwell et al. | |
| 2008/0119793 A1* | 5/2008 | Adams et al. | 604/174 |
| 2009/0120445 A1 | 5/2009 | Chikashige | |
| 2011/0098602 A1* | 4/2011 | Campbell et al. | 600/587 |

(Continued)

*Primary Examiner* — Nicholas Lucchesi
*Assistant Examiner* — Leah Stohr
(74) *Attorney, Agent, or Firm* — Woodard Emhardt Moriarty McNett & Henry, LLP (57) ABSTRACT

Devices, systems and methods are disclosed for providing a direct visual indication of the relative inflationary condition of the balloon on a balloon catheter after insertion into the patient. In certain exemplary embodiments, a gastrostomy tube catheter is disclosed having a fluid feeding lumen and a balloon inflation lumen, a balloon communicating with the balloon inflation lumen, and an indicator strip having one end fixedly attached to the balloon and a free end movable along the length of the tube in accordance with the relative inflation and deflation of the balloon. The presence of the free end of the strip along an exposed portion of the gastrostomy tube serves as a direct visual indicator of a deflated condition of the balloon.

1 Claim, 8 Drawing Sheets

(56) References Cited

U.S. PATENT DOCUMENTS

| | | | |
|---|---|---|---|
| 2011/0196341 A1* | 8/2011 | Howell | 604/514 |
| 2011/0220119 A1 | 9/2011 | Lowenstein et al. | |
| 2011/0270176 A1 | 11/2011 | Ehrenreich et al. | |
| 2011/0295236 A1 | 12/2011 | Gregory | |
| 2012/0078235 A1 | 3/2012 | Martin et al. | |
| 2012/0101515 A1 | 4/2012 | Barbod | |

* cited by examiner

VISUAL INFLATION/DEFLATION INDICATOR FOR A BALLOON CATHETER

CROSS-REFERENCE TO RELATED APPLICATION

This application claims the benefit of U.S. Provisional Application No. 61/700,056 filed Sep. 12, 2012, which is hereby incorporated by reference.

BACKGROUND

This disclosure pertains generally to the field of medical devices, and more particularly to balloon type catheters, and especially gastrostomy tube catheters, for insertion into the body of a patient.

There exists a variety of medical situations in which balloon catheters have been employed. Generally speaking, a balloon catheter refers to a catheter whose tip or forward portion has an inflatable balloon that either holds the catheter in place, such as for example in gastrostomy catheters used to provide nutritional feeding to a patient, or that can dilate the lumen of a blood vessel, such as for example in angioplastic procedures. In certain situations, it is particularly desirable to provide a direct visual indication to be able to verify the inflation and/or deflation condition of the balloon after the catheter has been inserted within the body of the patient and the balloon's condition can no longer be directly visually observed.

One particular situation where direct visual verification is especially desirable involves gastrostomy catheters (variously also referred to as gastrostomy tubes, G-tube catheters, PEG catheters, and enteral feeding tubes or catheters). These catheters often need to be maintained for long term use by the user or patient at home. Over time, the balloon may eventually weaken and develop a puncture, leak or other condition causing a loss of fluid pressure inside the balloon. If not discovered in a timely fashion, the balloon's deflation could result in the catheter being inadvertently removed.

Various methods and devices have been employed to provide a sensor or indicator useful for monitoring balloon pressure or the relative inflationary condition of the catheter balloon, but many suffer drawbacks in that they are too complicated, bulky, and/or expensive in their design and therefore not particularly suited for long term use, home use, and/or other situations. Thus, there is a need for improvement in this field and the present disclosure is directed to addressing those needs.

SUMMARY

In various aspects, the embodiments disclosed herein are directed to unique devices, methods and systems for directly visually indicating the relative inflation condition of a balloon catheter.

In one embodiment, a balloon catheter includes a tube having a main lumen and a balloon inflation lumen, a balloon communicating with the balloon inflation lumen, and an indicator strip having one end fixedly attached to the balloon and a free end movable along the length of the tube in accordance with the relative inflation and deflation of the balloon. The presence of the free end of the strip along an exposed portion of the tube serves as a visual indicator of a deflated condition of the balloon.

In another embodiment, a balloon catheter includes a gastrostomy tube having a fluid feeding lumen and a balloon inflation lumen, a balloon communicating with the balloon inflation lumen, and an indicator channel extending along the surface of the balloon and at least a portion of the tube. The indicator channel contains a liquid contrast media. The presence of the liquid contrast media along an exposed portion of the indicator channel serves as a visual indicator of a deflated condition of the balloon.

In yet another embodiment, a balloon catheter includes a gastrostomy tube having a fluid feeding lumen and a balloon inflation lumen, a balloon communicating with the balloon inflation lumen, and an indicator band substantially surrounding at least the exposed portion of the catheter. The indicator band has one end fixedly attached to the balloon and a free end movable along the length of the tube in accordance with the relative inflation and deflation of the balloon. The presence of the free end of the indicator band along an exposed portion of the tube serves as a visual indicator of a deflated condition of the balloon.

Additional embodiment summaries can be understood from reference to the claims hereinafter, with it being understood that each claim is considered an embodiment disclosed.

Further forms, objects, features, aspects, benefits, advantages, and additional embodiments of the present disclosure will be apparent to those skilled in the art from the detailed description and drawings included herein.

DETAILED DESCRIPTION

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Figure 1:
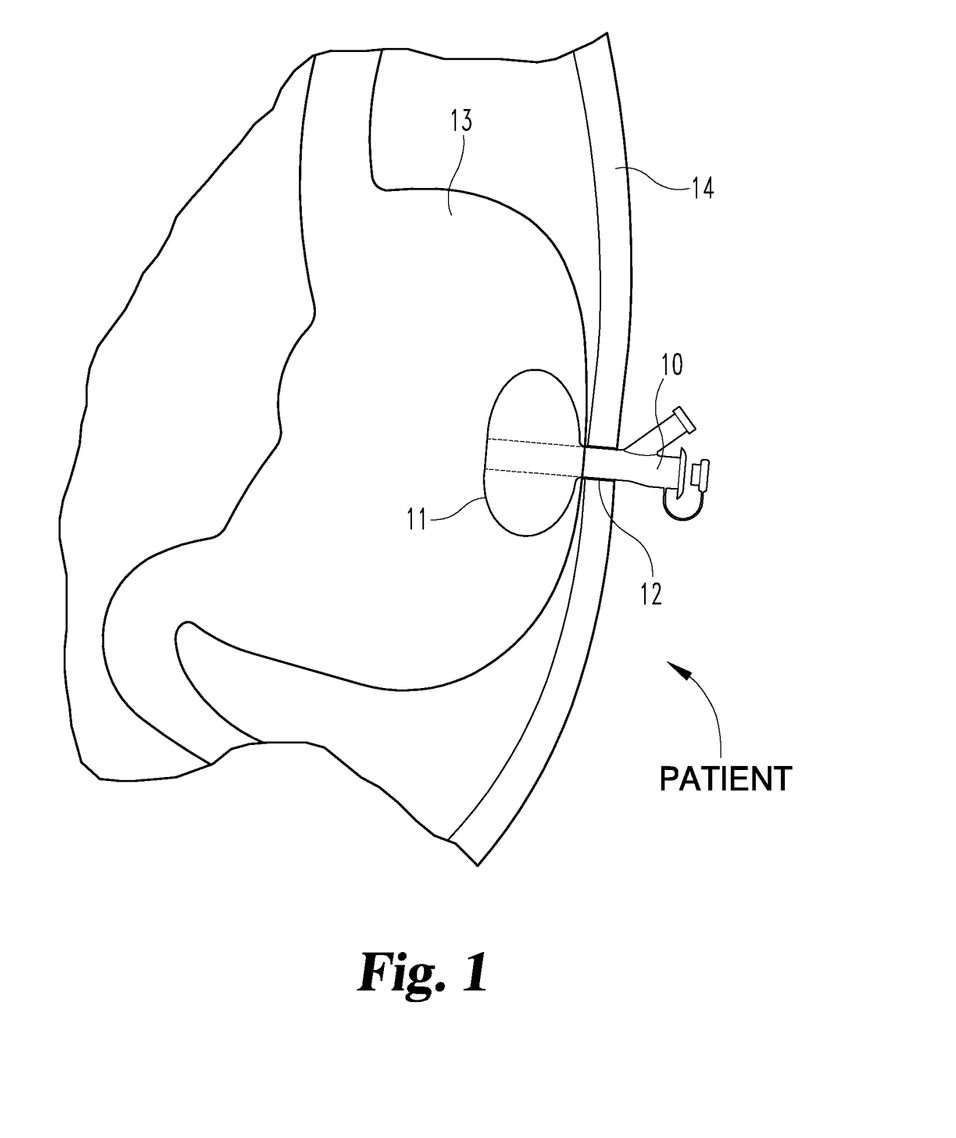
FIG. 1 illustrates one embodiment according to the present disclosure of a balloon type catheter with the balloon in an inflated condition inside the stomach of a patient.

Referring now to the drawings, there is shown in FIG. 1 a gastrostomy tube balloon catheter 10 implanted within the stomach of a patient such as for feeding of nutritional solutions or delivery of medicines to the stomach and intestines. It should be understood that while FIG. 1 depicts a gastrostomy tube balloon catheter, the present disclosure encompasses any other type of balloon in which there is a need to provide an external visual indicator of the inflation/deflation condition of the balloon inside the body. The catheter 10 is depicted with balloon 11 in its fully inflated condition serving as a retention system preventing unintended withdrawal of the catheter from the patient's stomach. The catheter 10 may be implanted using any one of a variety of methods including for example by percutaneous endoscopic gastrostomy (PEG). In this method, an endoscope is passed through the mouth, throat and esophagus into the stomach. The endoscope allows the doctor to choose the best location in the stomach to place the catheter 10. The physician then makes a stoma 12 through the abdominal wall 14 and stomach 13 and the catheter 10 is passed through the stoma 12 into the stomach 13. The balloon 11 is then inflated to retain the catheter 10 in place.

Figure 2:
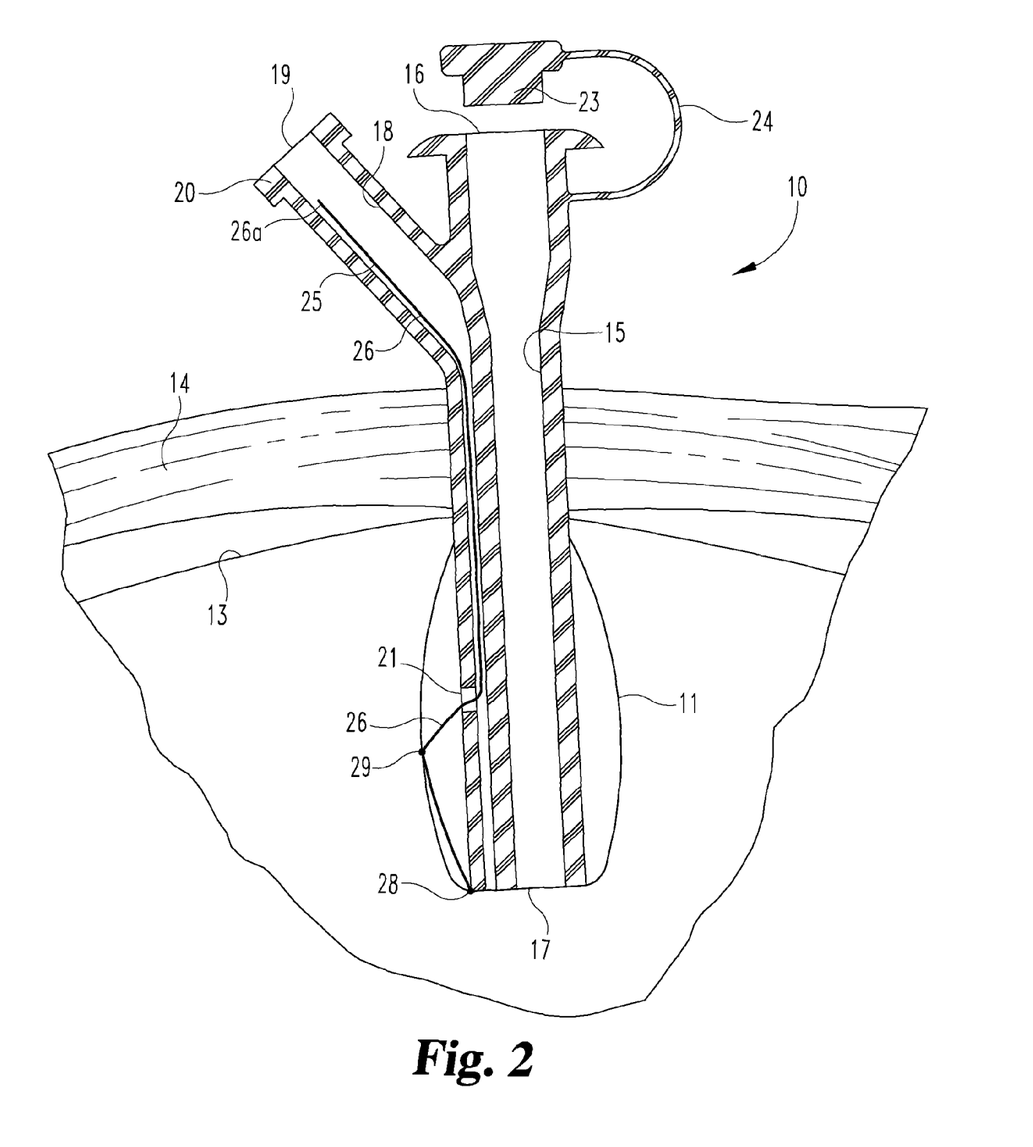
FIG. 2 illustrates an embodiment of a balloon type catheter in cross-sectional view with a visual inflation/deflation indicator indicating the deflated condition of the balloon.

In this illustrative embodiment as seen in FIG. 2, the catheter 10 includes a main lumen 15 extending axially between proximal and distal open ends 16 and 17, respectively. The main lumen 15 is sized to permit delivery of nutrient solution feedings therethrough directly into the patient's stomach. Balloon 11 is situated towards the distal end 17 and communicates with an inflation lumen 18. The catheter 10 includes an inflation port 19 in fluid communication with the balloon 11 through inflation lumen 18 separate from the main lumen 15. An opening 21 in lumen 18 is provided in the outer wall of the catheter 10 to allow inflation and deflation of the balloon 11 by operation of a valve 20 controlling the opening and closing of the inflation port 19. A removable cap 23 is provided to seal the proximal open end 16 of the catheter 10 during periods between feedings. A flexible strap 24 attaches cap 23 to catheter 10.

Figure 3:
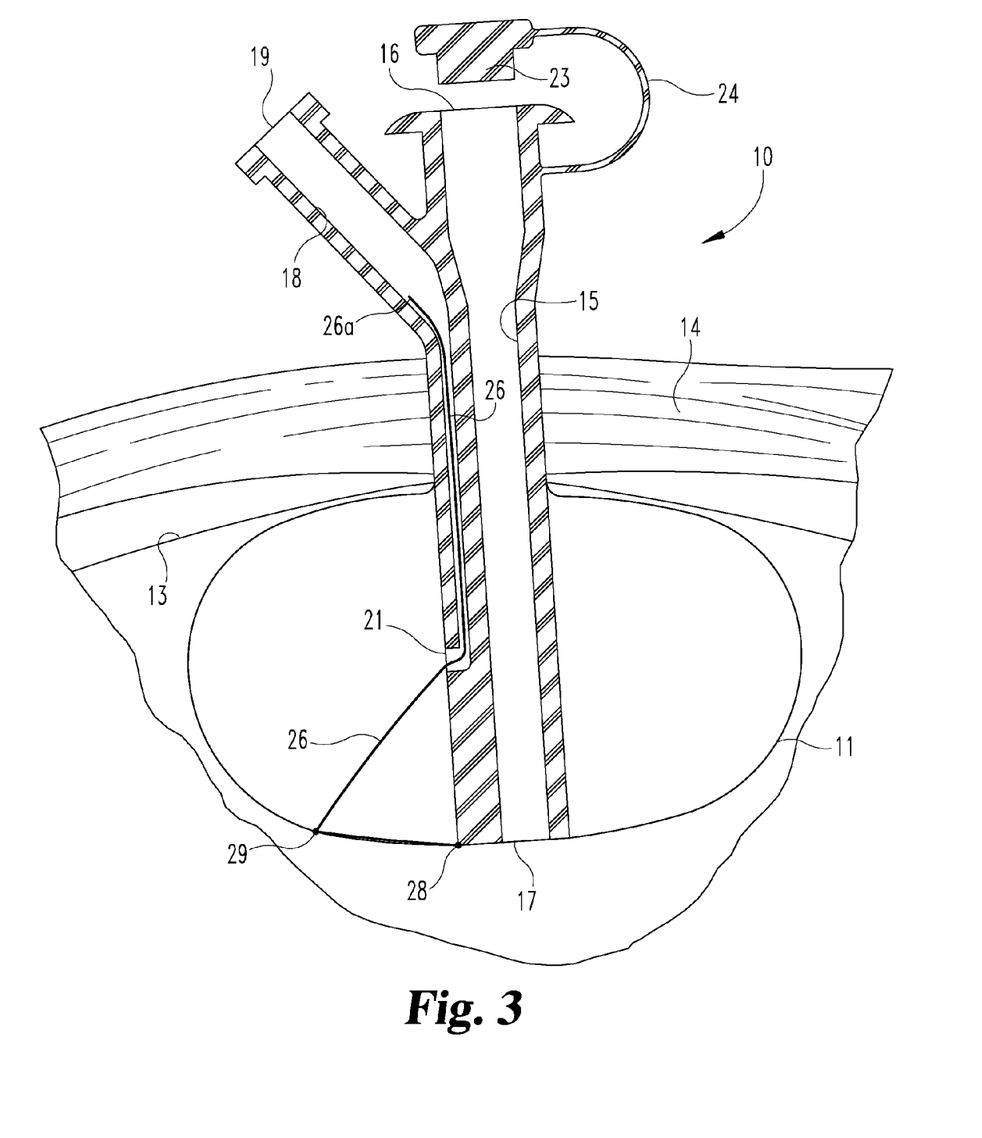
FIG. 3 illustrates the embodiment of FIG. 2, but with the visual inflation/deflation indicator indicating the inflated condition of the balloon.

In order to allow the user or physician to verify that the balloon 11 is properly inflated, the catheter 10 is provided with a visual inflation/deflation indicator device 25. As seen in FIGS. 2 and 3, the visual indicator device 25 is preferably in the form of a thin flat indicator strip 26 having a predetermined fixed length. As understood herein, the term "strip" is defined broadly to include any long and relatively narrow piece, body or component, including but not limited to a string, cord, filament, thread, line, wire, cable, braid, ribbon, tape, or band. Indicator strip 26 is attached to the balloon 11 at a first location 28 preferably positioned near the distal or forward end thereof and at a second location 29 intermediately positioned along the length of balloon 11. Alternately, it should be understood that indicator strip 26 could be attached to more than two locations or even attached along the entire length thereof between locations 28 and 29. The indicator strip 26 may for example be made of a suitable biocompatible material having the desired flexibility and strength characteristics to allow it to freely move as desired without becoming distorted, twisted or stretched.

Figure 4:
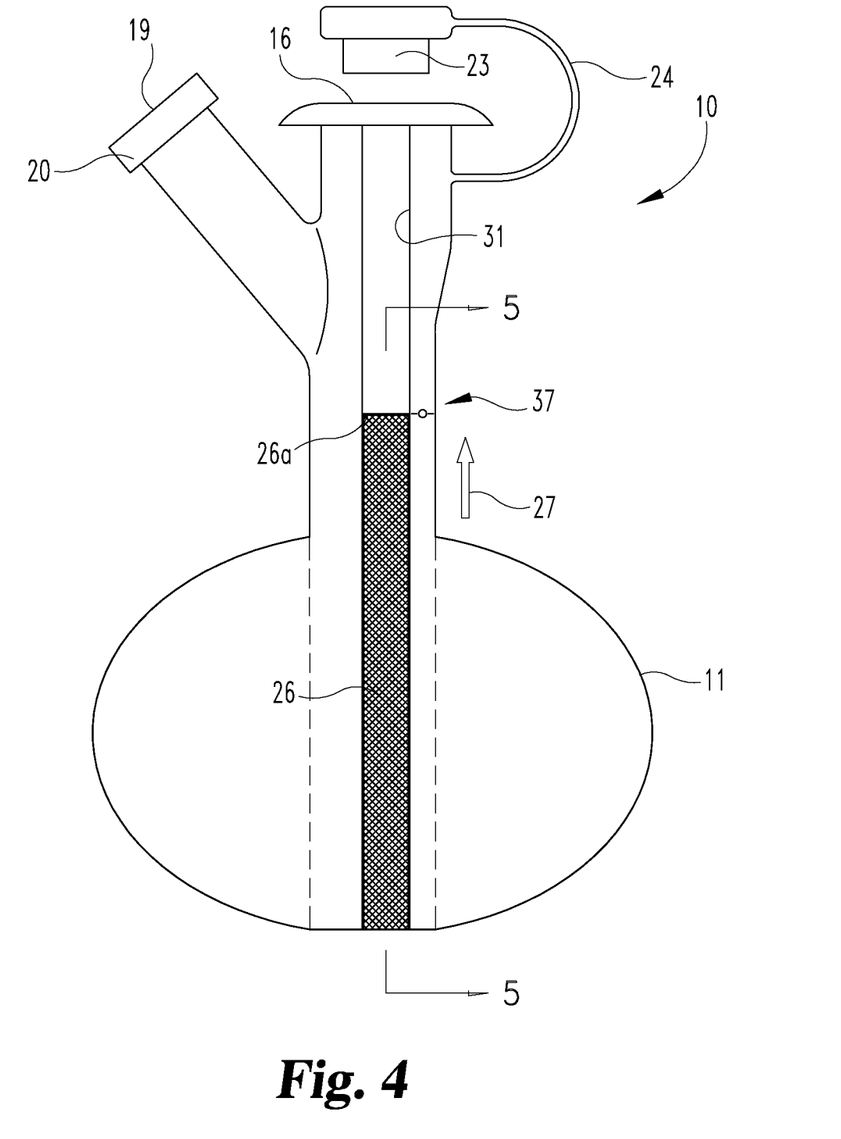
FIG. 4 illustrates an alternate embodiment of a balloon type catheter in elevation view with a visual inflation/deflation indicator.

From location 29, the indicator strip 26 freely extends into the inflation lumen 18 as seen in FIGS. 2 and 3. Alternately, as seen in FIG. 4, the catheter 10 may have a channel 31 provided separate from the inflation lumen 18 formed in or on the outer surface of the catheter 10 and balloon 11. In either case, the indicator strip 26 is freely movable axially inside the inflation lumen 18 or channel 31 in accordance with the relative inflation and deflation of the balloon 11. Since the indicator strip 26 has a fixed length, as the balloon 11 expands outwardly while being inflated the free end 26a of the indicator strip 26 will move in the direction opposite of arrow 27 until it reaches the position shown in FIGS. 3-5 corresponding to the fully and properly inflated condition of balloon 11.

Figure 5:
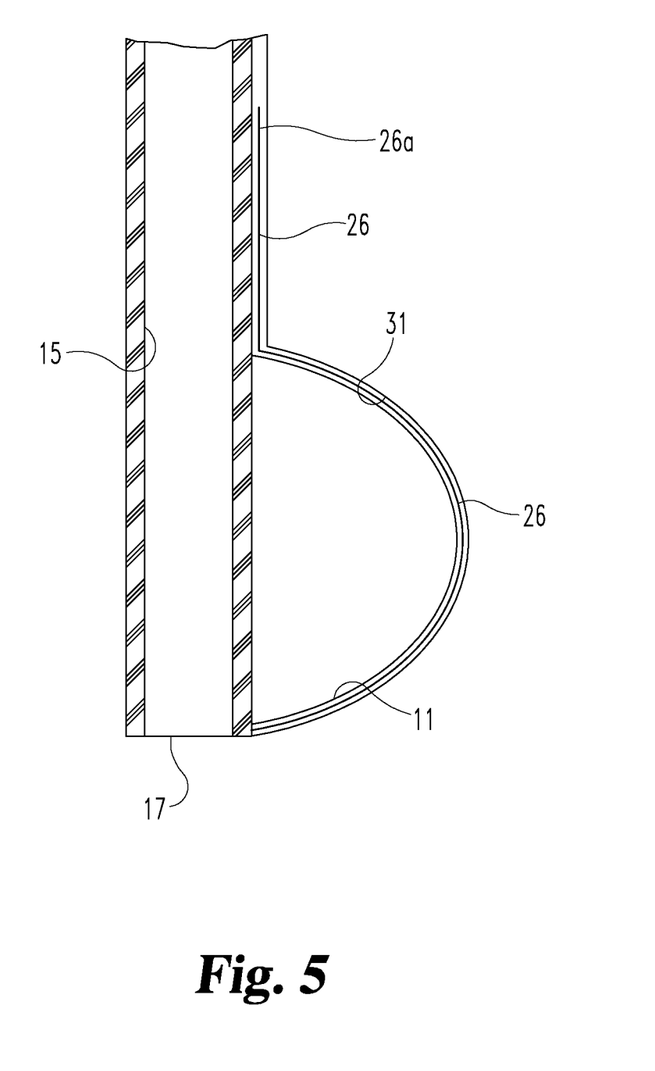
FIG. 5 is a partial cross-section taken along lines 5-5 in FIG. 5.

If balloon 11 is then deflated, the free end 26a of the indicator strip 26 will move in a direction along the direction of arrow 27 towards the position shown in FIG. 2 corresponding to the fully deflated condition of balloon 11. Thus, as depicted in FIG. 2, the presence of the indicator strip 26 along a portion of the catheter 10 extending outside of the patient serves as a direct visual indication that balloon 11 has suffered a rupture or leak and is no longer properly inflated. Conversely, as depicted in FIGS. 3-5, the absence of or retraction of the indicator strip 26 along the portion of the catheter 10 extending outside of the patient serves as a direct visual indication that balloon 11 has not suffered any rupture or leak and is properly inflated.

Figure 8:
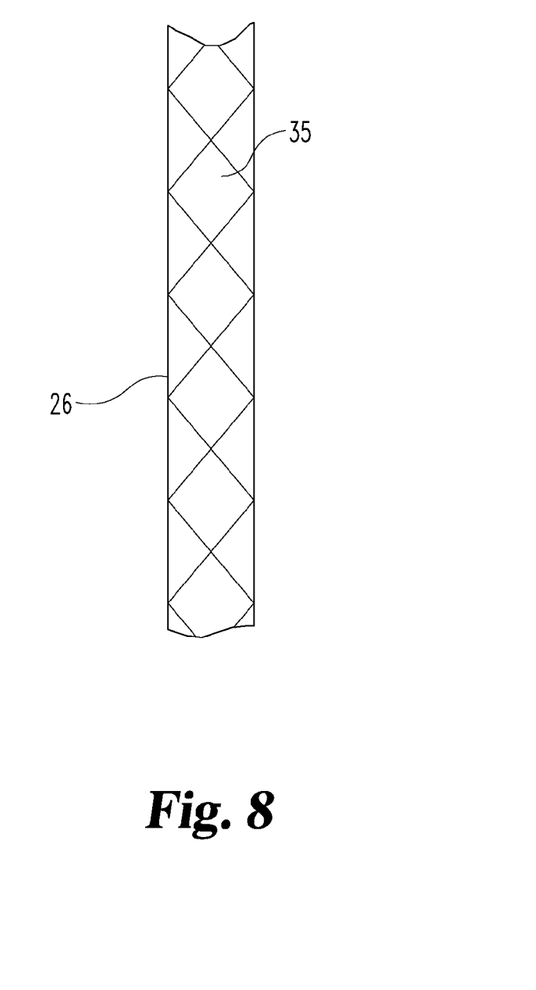
FIGS. 8 and 9 depict exemplary forms of markings to aid visualization of the inflation/deflation indicator.
Figure 9:
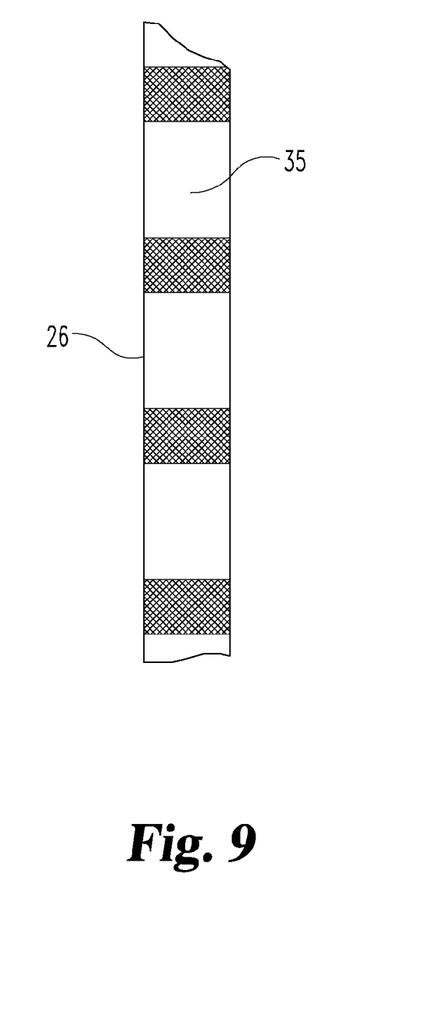

In order to aid visualization of the indicator strip 26, the strip 26 is shown highlighted with a visually contrasting color relative to the catheter 10, which may itself be made of a substantially transparent or translucent material to allow as desired in order to facilitate visualization of indicator strip 26. Alternately, or in combination therewith, strip 26 may be provided with distinctive markings or patterns 35 such as depicted in FIGS. 8 and 9. Optionally, as seen in FIG. 4, marking indicia 37 may also be placed along the outer surface of the catheter 10 to aid in the visualization of the inflated/deflated positions of the indicator strip 26. Marking indicia 37 may optionally be placed at multiple locations along catheter 10, including marking the fully inflated, fully deflated, and one or more intermediate locations indicating partially inflated/deflated conditions of balloon 11 so that the indicator strip 26 is also able to indicate a potential failure (e.g., slow leak) versus a full failure.

Figure 6:
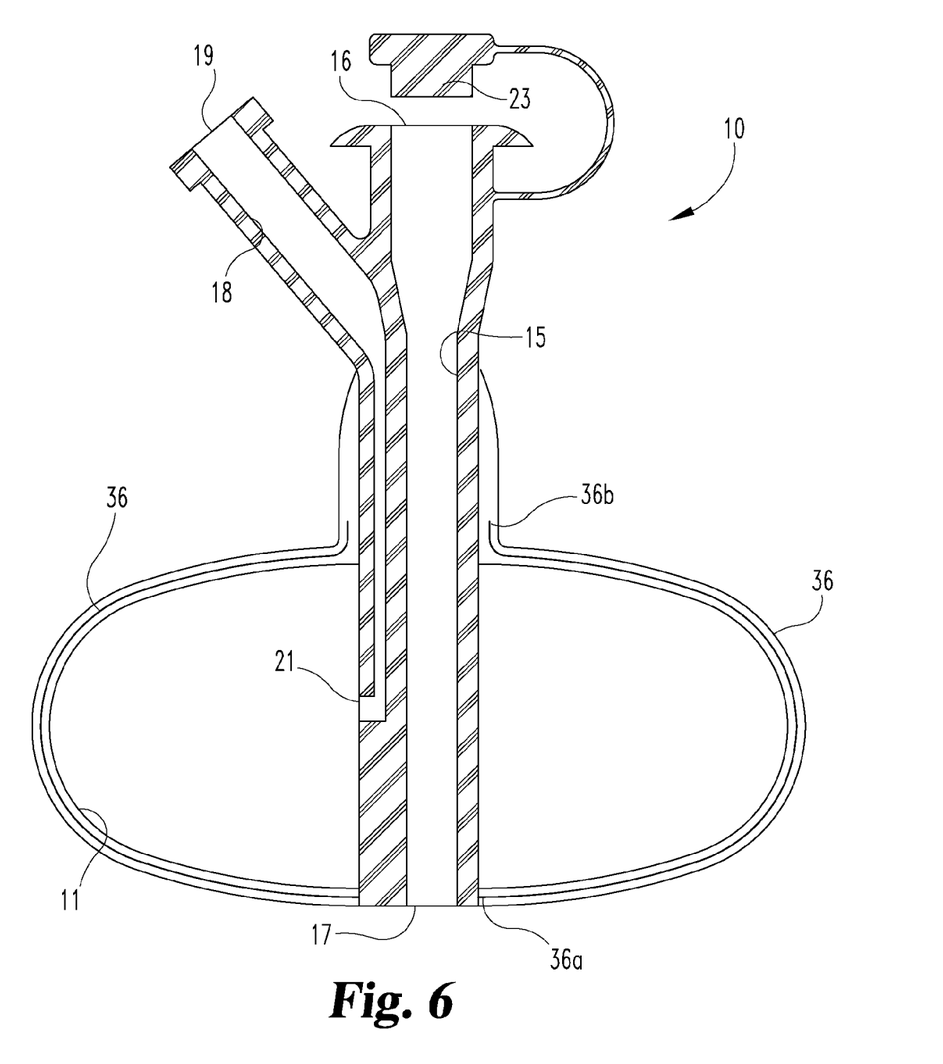
FIGS. 6 and 7 illustrate further embodiments of a balloon type catheter in cross-sectional views with a visual inflation/deflation indicator indicating the deflated condition of the balloon.
Figure 7:
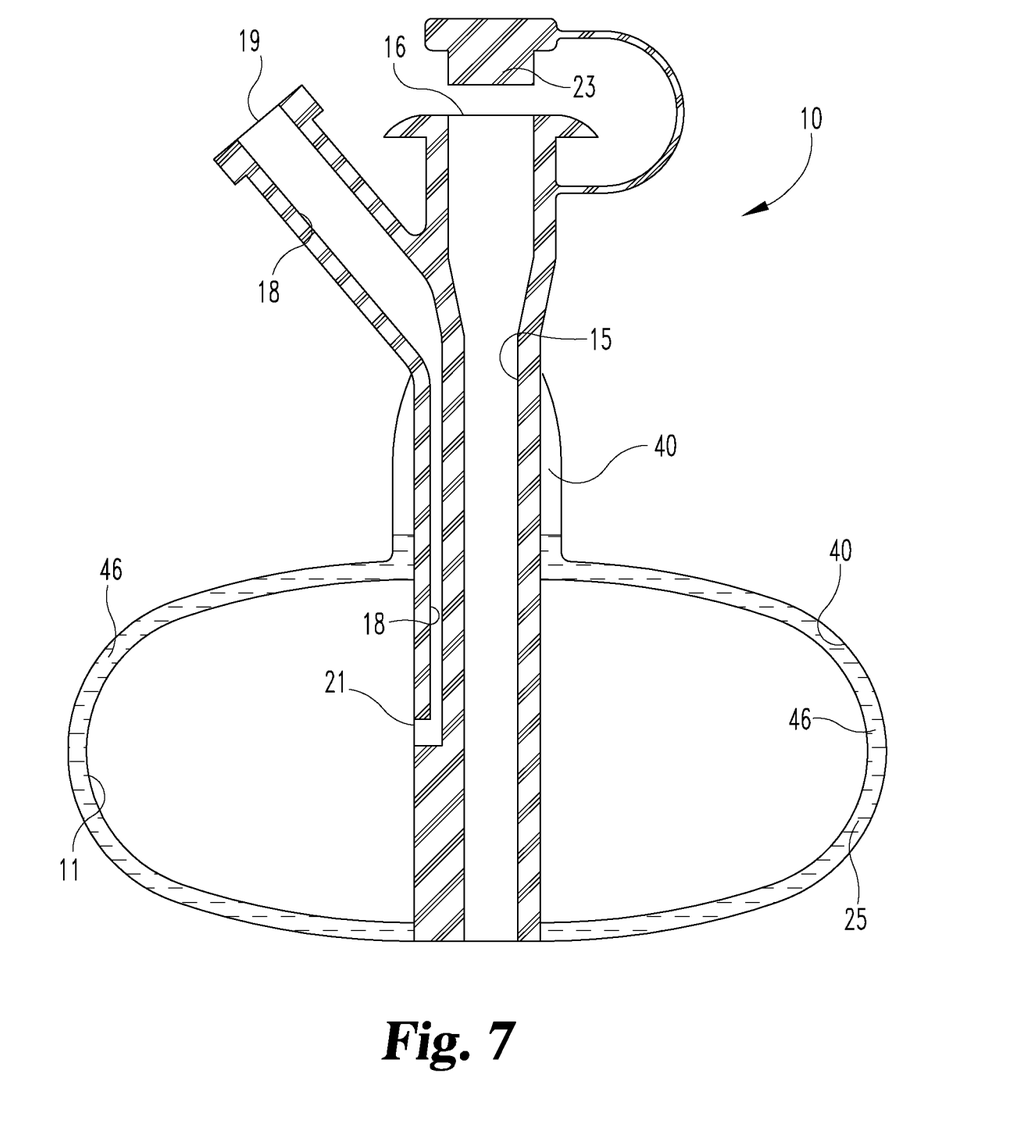

FIGS. 6 and 7 depict further alternate embodiments of the visual inflation/deflation indicator device 25 of catheter 10. In both FIGS. 6 and 7, the balloon of catheter 10 is shown in its inflated condition. As seen in FIG. 6, the device 25 comprises an indicator band 36 of fixed predetermined length substantially surrounding the balloon 11 somewhat akin to a blanket. As in the previous embodiments, the indicator band 36 has one end 36a fixedly attached to the balloon and extends in a channel formed on the surface of the balloon 11 and catheter 10. The free end 36b of the indicator band 36 is movable along an exposed portion of the length of the catheter 10 in accordance with the relative inflation and deflation of the balloon 11. The presence of the free end of the indicator band 36 along an exposed portion of the catheter 10 serves as a direct visual indicator of a deflated condition of the balloon 11.

A yet further embodiment of the visual inflation/deflation device 25 is depicted in FIG. 7. In this embodiment, the visual inflation/deflation device 25 comprises an indicator channel 40 containing liquid contrast media 46. The indicator channel 40 is formed upon and extends along the surface of the balloon 11 and at least an exposed portion of the catheter 10. As depicted in FIG. 7, the indicator channel 40 substantially surrounds the balloon 11 and catheter 10. The space within indicator channel 40 contains the liquid contrast media 46, which may for example be colored water. Inflation of the balloon 11 expands the volume of the portion of the indicator channel 40 extending along balloon 11 and causes the level of the liquid contrast media 46 within indicator channel 40 to drop until it is no longer visible along the exposed portion of catheter 10 extending outside the body of the patient. The presence of the liquid contrast media 46 along a portion of the indicator channel 40 extending outside the body of the patient thus serves as a direct visual indicator of a deflated condition of the balloon 11.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are indicative of the level of skill in the art and are hereby incorporated by reference as if each individual publication, patent, or patent application were specifically and individually indicated to be incorporated by reference and set forth in its entirety herein. In addition, all references cited herein are indicative of the level of skill in the art and are hereby incorporated by reference in their entirety.

The invention claimed is:

1. A gastrostomy apparatus, comprising:
    a tube having a fluid feeding lumen and a balloon inflation lumen;
    a balloon communicating with the balloon inflation lumen; and
    an indicator channel extending along the surface of the balloon and at least a portion of the tube, the indicator channel containing a liquid contrast media not in fluid communication with the balloon, wherein the presence of the liquid contrast media along an exposed portion of the indicator channel serves as a direct visual indicator of a deflated condition of the balloon.

* * * * *